United States Patent [19]

Schneider

[11] 4,320,239

[45] Mar. 16, 1982

[54] REACTION PRODUCTS OF AN OLEFIN, A NORBORNENE AND A CYCLOPENTADIENE

[75] Inventor: Wolfgang Schneider, Broadview Heights, Ohio

[73] Assignee: The B. F. Goodrich Company, Akron, Ohio

[21] Appl. No.: 234,277

[22] Filed: Feb. 13, 1981

[51] Int. Cl.$^3$ .................. C07C 13/42; C07C 13/48
[52] U.S. Cl. ................. 585/360; 585/362; 585/350
[58] Field of Search .............. 585/350, 360, 362

[56] References Cited

U.S. PATENT DOCUMENTS

| | | | |
|---|---|---|---|
| 3,183,249 | 5/1965 | Wiese | 585/360 X |
| 3,470,142 | 9/1969 | Sartori et al. | 585/360 X |
| 3,557,072 | 1/1971 | Vergne et al. | 526/169 X |
| 3,953,534 | 4/1976 | Sundt | 585/360 X |
| 4,207,080 | 6/1980 | Suld et al. | 585/362 X |

OTHER PUBLICATIONS

Wiberg et al., CA 74: 53135g (1971).

*Primary Examiner*—Thomas A. Waltz
*Attorney, Agent, or Firm*—George A. Kap; Nestor W. Shust

[57] ABSTRACT

A product mixture of a norbornene and a tetracyclododecene is prepared in any desired mole ratio in the range of 95/5 to 5/95 which comprises heating an olefin, cyclopentadiene, and a norbornene in the respective mole ratio of 1-20/1-5/1-5, at a temperature of 100° to 400° C., 100 to 5000 psi, and 0.1 to 5 hours of residence time.

12 Claims, 8 Drawing Figures

REACTION PRODUCTS OF AN OLEFIN, A NORBORNENE AND A CYCLOPENTADIENE

BACKGROUND OF THE INVENTION

Useful polymeric products are obtained by polymerizing a norbornene and a tetracyclododecene with or without cyclopentadiene and/or other copolymerizable monomers. Such polymeric products can be either elastomeric or rigid plastics, depending on what reactants are employed and on formulation of such polymeric products.

Norbornene or an alkylnorbornene can be prepared in a known manner by reacting on olefin with cyclopentadiene. The reaction mixture is distilled to separate norbornene and high boilers, the latter being mostly trimers of cyclopentadiene. Tetracyclododecene, as well as alkyltetracyclododecene, can be prepared by reacting a norbornene and cyclopentadiene. The product of this reaction contains tetracyclododecene, unreacted norbornene, and high boilers along with a small portion of unreacted cyclopentadiene.

SUMMARY OF THE INVENTION

This invention relates to a single-step process for preparing a norbornene and a tetracyclododecene by reacting an olefin, a norbornene, and a cyclopentadiene. Relative proportion of norbornene to tetracyclododecene in the product mixture is controlled by varying relative amounts of the reactants whereby molar ratio of norbornene to tetracyclododecene of 95/5 to 5/95 is obtained in the product mixture. The product mixture is then distilled to recover norbornene and tetracyclododecene leaving high boilers behind. To complete the process, a portion of norbornene can be recycled to the reaction vessel to serve as a reactant.

DETAILED DESCRIPTION OF THE INVENTION

Figure 1:
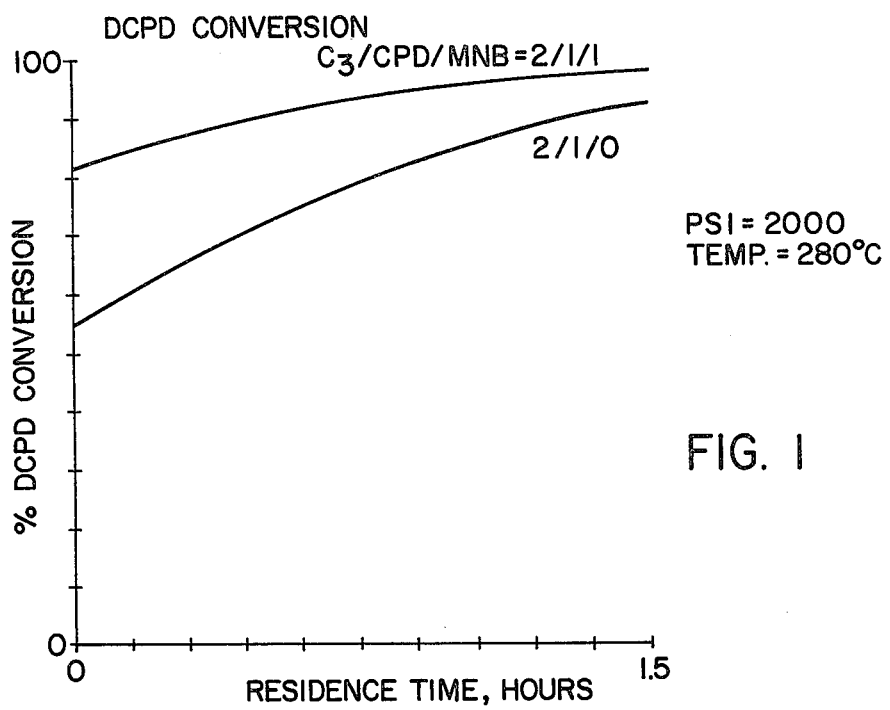
FIG. 1 is a graph of dicyclopentadiene (DCPD) conversion plotted against residence time at reaction conditions of 280° C., 2000 psi and propylene/cyclopentadiene/methylnorbornene (C₃/CPD/MNB) mole ratios of 2/1/0 and 2/1/1.

Pursuant to this invention norbornene and tetracyclododecene can be produced in a single-step process in any desired molar ratio ranging from 95/5 to 5/95. If desired, an excess amount of norbornene can be produced by this process for recycling to the reaction vessel in order to maintain continuous operation of the process.

The process of this invention is carried out by reacting an olefin, a norbornene, and cyclopentadiene to produce tetracyclododecene, norbornene, and high boilers. It should be understood that substituted cyclopentadienes can also be used in place of cyclopentadiene. Presently, only dimethyldicyclopentadiene is available commercially. Most of the high boilers are trimers of cyclopentadiene. Relative ratio of the reactants can vary as follows: 1 to 20, preferably 2 to 10 moles of the olefin; 1 to 5 moles of cyclopentadiene, or one-half of this amount of dicyclopentadiene; and 1 to 5 moles of the norbornene. This reaction, which is not balanced, is represented as follows:

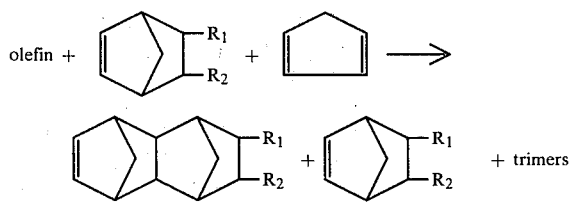

wherein $R_1$ and $R_2$ are independently selected from hydrogen and alkyl or alkylene groups of 1 to 20 carbon atoms, provided that the total number of carbon atoms of $R_1$ and $R_2$ does not exceed 20; preferably $R_1$ and $R_2$ are independently selected from alkyl and alkylene groups of 1 to 10 carbon atoms, and most preferably from alkyl groups of 1 to 2 carbon atoms; or $R_1$ and $R_2$, together with the ring carbons to which they are bonded, form one or more, preferably one or two, saturated or unsaturated rings of 6 to 16 carbon atoms, preferably 6 to 10 carbon atoms. In a preferred embodiment, one of $R_1$ and $R_2$ is hydrogen whereas the other is as defined above.

Depending on the olefin employed, the resulting norbornene derivative will be a monoalkyl, a monoalkylene, a dialkyl, a monoalkyl-monoalkylene, a dialkylene, or a cyclic derivative. More specifically, if the olefin employed is an aliphatic alpha-monoolefin, then a monoalkyl derivative is obtained. When an internal olefin is employed, i.e., an olefin which contains unsaturation on other than an alpha-carbon, the resulting product is a dialkyl derivative. A monoalkylene derivative of norbornene is obtained when the olefin used in the reaction is a diolefin with one unsaturation on the alphacarbon and a dialkylene derivative is produced when the three unsaturations are internal.

Suitable olefins are aliphatic and cyclic olefins containing 2 to 22 carbon atoms, preferably 2 to 12 and especially 2 to 4 carbon atoms. Typical examples of aliphatic alpha-olefins are ethylene, propylene, butene, pentene, hexene, octene, decene, dodecene, tetradecene, octadecene, and the like. Typical examples of diolefins include butadiene -1,2, butadiene -1,3, pentadiene -1,2, pentadiene -1,3, pentadiene -1,4, hexadiene -1,2, hexadiene -1,4, and the various isomers of heptadiene, octadiene, decadiene, dodecadiene, hexadecadiene, octadecadiene, and the like. Suitable examples of the internal olefins include butene -2, pentene -2, hexene -2, hexene -3, heptene -2, heptene -3, octene -2,3, and 4, decene -2,3,4, and 5, dodecene -2 to 6, and the like. Typical examples of cyclic olefins include cyclooctadiene, cyclooctene, cyclopentene, cyclohexene, cyclododecatriene, and the like.

The process of this invention can be carried out at a temperature of about 100° to 400° C., preferably at 200° to 300° C. It was found that at temperatures below about 200° C., selectivity and conversion become progressively lower requiring increased residence time whereas at temperatures above about 300° C., the undesirable polymer buildup increases which causes eventual plugging of the reactor and the associated equipment. Residence time can generally be varied in the range of about 0.1 to 5 hours, however, from the standpoint of improved selectivity and conversion, it is preferred to hold residence time between 0.5 and 2 hours. The process is generally carried out at a pressure sufficient to maintain the reaction in liquid phase. The pressure is in the range of 100 to 5000 psig, preferably 500 to 4000 psig.

Selectivity of norbornene and tetracyclododecene products depends mainly on the ratio of the reactants. Generally speaking, a high level of an olefin favors formation of a norbornene whereas an excess amount of a norbornene reactant favors formation of a tetracyclododecene. Therefore, to obtain a product mixture composed mostly of a tetracyclododecene, amount of olefin should be reduced whereas amount of dicyclopentadiene should be increased. It should be understood that under these conditions, proportion of trimers will increase accordingly. In the case where a preponderance of a norbornene is desired in the product mixture, an excess of olefin should be used. This condition will lead to formation of reduced amounts of the trimers.

In place of cyclopentadiene hydrocarbons, it is also suitable to use dimers of cyclopentadiene such as dicyclopentadiene and dimethyldicyclopentadiene. It should be understood that although a dimer may be charged into a reaction vessel, it is the monomeric cyclopentadiene that enters into the reaction. The dimers easily depolymerize to the monomers under the reaction conditions.

The product mixture is distilled to recover norbornene and tetracyclododecene and thus separate these monomers from high boilers. Norbornene and tetracyclododecene are separated from the reaction mixture in a certain mole ratio with a portion of norbornene being recycled, if desired, and remainder can be polymerized with tetracyclododecene in any desired mole ratio, with or without cyclopentadiene or any other copolymerizable monomer such as styrene, acenaphthylene, etc., as is well known in the art. Polymerization can be carried out in a known manner, as is disclosed in U.S. Pat. No. 3,557,072. The mole ratio of norbornene and tetracyclododecene can be varied widely by varying mole ratio of the reactants. This means that a mole ratio of norbornene to tetracyclododecene in the product mixture can be produced which would provide sufficient norbornene and tetracyclododecene for polymerization to useful products and just the right amount of excess norbornene for recycling so that the process can be operated on a continuous basis. Recycling of norbornene is necessary since it is not readily available.

More specifically, the reaction procedure involves preblending in a feed tank an aliphatic olefin, a norbornene such as methylnorbornene, and cyclopentadiene. A known amount of m-xylene, on the order of about 5% by weight of reactants, is added to the reactants as an internal standard for gas chromatographic analyses. The feed tank is pressured with a blanket of 150-200 psi nitrogen to convey the feed in liquid phase to a weighing bomb disposed on a scale. A metering pump conveys the feed from the weighing bomb to an autoclave by means of a dip tube and the reaction products and unreacted feed are conveyed from the autoclave through the autoclave head. An impeller driven by an air motor agitates the reaction mixture.

The autoclave is a continuous flow, stirred tank reactor equipped with a pressure gauge, a vent line with a rupture disk, and a thermocouple which controls the heating jacket surrounding the reactor. After the reaction mixture leaves the reactor, it is cooled and depressurized through a back pressure regulator to 100 psi and through a second back pressure regulator to atmospheric pressure. A sampling device is installed between the two back pressure regulators.

Operation of the reactor is conducted by allowing it to run uninterrupted for several residence times to reach steady state. After steady state is established, three double samples are taken, each double sample being taken one residence apart. A one milliliter sample is injected under pressure with a needle through the septum cap of a two milliliter vial. The vials are kept cool in dry ice prior to the gas chromatographic analyses.

The time it takes a molecule to pass through a reactor is called its residence time. Since different molecules stay different lengths of time in the reactor, the mean residence time is averaged for all the elements of a fluid.

The products obtained by polymerizing a norbornene and a tetracyclododecene with or without dicyclopentadiene and any other copolymerizing monomer can be elastomers or engineering thermoplastics. The engineering plastics are highly desirable materials which have some outstanding properties such as heat distortion temperature in the range of 110° to 170° C., glass transition temperature of 100° to 200° C., high hydrolytic stability, low specific gravity, good electrical properties, and others. Some of the specific applications of such engineering thermoplastics include battery housings, power tool parts, TV parts, parts for small appliances and microwave ovens, as potting compounds, etc. These specific items can be produced either by cold-forming or by injection molding.

EXAMPLE I

Numerous reactions were carried out at various reaction conditions to prepare methylnorbornene (MNB) and methyltetracyclododecene (MTD), in the manner described above. The first series of reactions involved a feed consisting of propylene ($C_3$) and dicyclopentadiene (DCPD) in a mole ratio of 5/1. These reactions produced a large amount of methylnorbornene, about 80% to 90% of the product, the remainder being methyltetracyclododecene and high boilers, the latter being essentially trimers of cyclopentadiene (trim.). By using a feed consisting of propylene, dicyclopentadiene, and methylnorbornene, it was possible to produce larger amounts of methyltetracyclododecene. Two additional feeds of $C_3$/CPD/MNB were prepared with mole ratios of 2/1/1 and 5/1/1. the 2/1/1 feed gave an MNB/MTD selectivity ratio of about ½ whereas the 5/1/1 feed gave a selectivity of about 2/1. The other variables, i.e., temperature, pressure, and residence time had a lesser effect on the selectivity ratio but a very substantial effect on DCPD conversion and on the formation of the undesirable high boilers, i.e., trimers and polymers. Results of these experiments confirm that a high DCPD conversion and a low selectivity for high boilers can be achieved by variations in temperature, pressure, and residence time. It appears that the use of excess amount of an olefin and/or a norbornene in the feed acts as a solvent and lowers formation of the high boilers. Results of these experiments are presented in the table below where amounts are given in moles or mole percent:

mole percent, as well as a trace of MHH and TET. The symbol (—) represents loss of MNB and means that MNB was lost due to polymerization or some other way. MNB recovery of 110.2 mole percent represents that 10.2 mole percent of new MNB was formed during the reaction.

EXAMPLE 2

Dozens of experiments were carried out to determine the effect of varying mole ratio of the reactants and reaction variables on reaction products. The experiments cover a wide range of reaction variables including pressures of 1000 to 3000 psi; C$_3$/CPD/MNB mole ratios of 1/1/0, 2/1/0, 5/1/0, 2/1/1, and 5/1/1; and residence time from 0.2 hour to 1.6 hours. FIGS. 1 to 8 are graphs of the various variables tested and present

TABLE I

| Pressure | Temp. °C. | R.T. | Conversion DCPD | Mole %, MNB | Products, Mole % MTD | Trim | MHH | Tet | Recovery MNB, Mole % |
|---|---|---|---|---|---|---|---|---|---|
| Feed Ratio: 5C$_3$:1CPD | | | | | | | | | |
| 1000 | 204 | 0.51 | 35.8 | 85.7 | 5.1 | 9.2 | . | . | |
| 1000 | 208 | 0.51 | 29.9 | 83.4 | 4.7 | 11.9 | . | . | |
| 1000 | 276 | 0.35 | 36.3 | 90.8 | 4.5 | 4.7 | . | . | |
| 1000 | 276 | 0.71 | 47.4 | 88.0 | 7.4 | 4.7 | . | . | |
| 1000 | 311 | 0.35 | 56.0 | 93.0 | 5.3 | 2.1 | . | . | |
| 1000 | 311 | 0.39 | 50.1 | 92.1 | 5.5 | 2.4 | . | . | |
| 2000 | 263 | 0.84 | 84.0 | 88.5 | 9.6 | 1.6 | . | . | |
| 3000 | 309 | 0.29 | 88.4 | 90.1 | 7.5 | 2.4 | . | . | |
| 3000 | 315 | 0.33 | 87.9 | 89.5 | 7.1 | 3.4 | . | . | |
| Feed Ratio: 2C$_3$:1CPD:1 MNB | | | | | | | | | |
| 1000 | 231 | 1.36 | 76.0 | 29.3 | 55.0 | 6.6 | 7.5 | 1.6 | 110.2 |
| 1000 | 240 | 0.31 | 53.0 | 20.2 | 58.4 | 12.3 | 7.2 | 1.9 | 104.7 |
| 1000 | 256 | 0.64 | 63.0 | (—) | 42.2 | 26.7 | 10.1 | 21.0 | 53.8 |
| 2000 | 255 | 1.57 | 91.0 | 26.8 | 56.1 | 6.7 | 6.8 | 3.6 | 111.3 |
| 3000 | 278 | 0.23 | 82.4 | 29.6 | 63.0 | 8.0 | 6.4 | 3.0 | 111.8 |
| 3000 | 296 | 0.23 | 81.7 | 13.6 | 58.3 | 13.6 | 7.9 | 6.6 | 104.6 |
| 3000 | 317 | 0.23 | 76.8 | (—) | 51.7 | 26.4 | 9.3 | 12.6 | 83.8 |
| Feed Ratio: 5C$_3$:1CPD:1 MNB | | | | | | | | | |
| 3000 | 236 | 1.41 | 91.5 | 58.1 | 24.9 | 11.5 | 1.9 | 3.6 | 128.5 |
| 3000 | 255 | 0.29 | 75.9 | 79.2 | 18.0 | 2.1 | 1.4 | 0.3 | 142.0 |
| 3000 | 276 | 0.29 | 82.8 | 76.6 | 19.1 | 2.3 | 1.3 | 0.7 | 144.1 |
| 1000 | 236 | 0.30 | 79.0 | 54.1 | 34.9 | 5.8 | 4.1 | 1.1 | 177.8 |
| 1000 | 281 | 1.23 | 89.5 | 56.8 | 30.8 | 7.7 | 2.4 | 2.3 | 116.1 |

. Trace amount
(—) Loss of MNB
R.T. Residence time

The abreviations used in the above table are identified in Table II, below, with additional information given for the reactents and products used in the inventive process:

TABLE II

| Abbreviation | Common Name | Molecular Weight | Boiling Point °C. | Density gm/ml |
|---|---|---|---|---|
| C$_3$ | propylene | 42.1 | −47 | 0.519* |
| CPD | cyclopentadiene | 66.1 | 42 | 0.802 |
| DCPD | dicyclopentadiene | 132.2 | 170 | 0.976 |
| MNB | methylnorbornene | 108.2 | 117 | 0.865 |
| MTD | methyltetracyclododecene | 174.3 | 225 | 0.989 |
| Trim | tricyclopentadiene | 198.3 | 240 | 0.97 |
| TET | tetracyclopentadiene | 264.4 | 160/1 mm | 1.0 |
| MHH | methylhexacycloheptadecene | 240.4 | 130/0.5 mm | |

*liquid at saturation pressure and 20° C.

Table I, above, reveals that a feed of 5C$_3$/1CPD mole ratio was reacted at 204° C. and 1000 psi at a mean residence time of 0.51 hour. Conversion of DCPD was 35.8 mole percent, and that of MNB, MTD, Trim, MHH, and TET was respectively 85.7, 5.1, and 9.2 data of the numerous experiments in graphic form.

Figure 2:
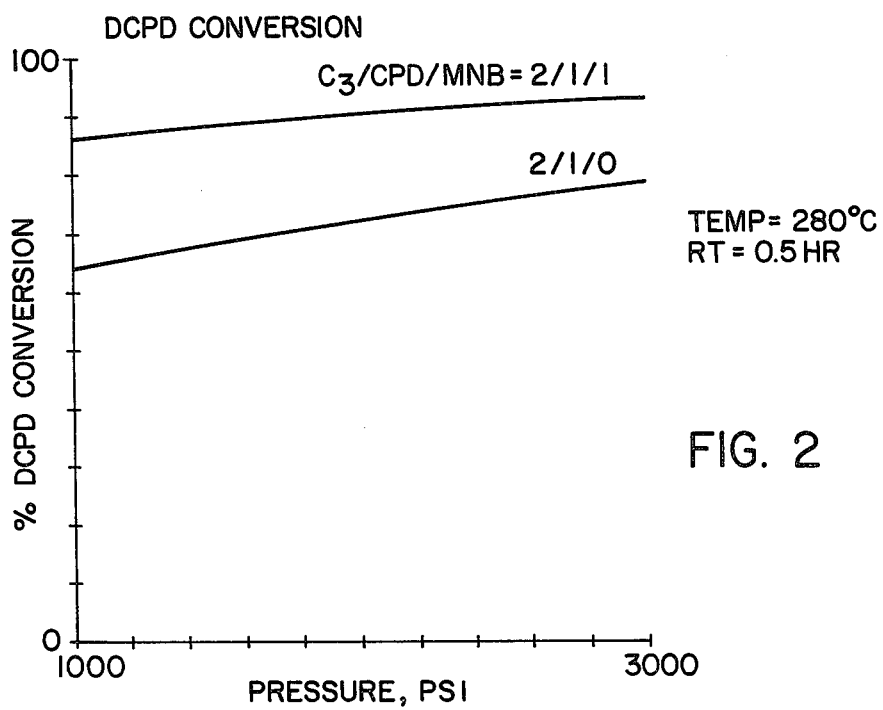
FIG. 2 is a graph of DCPD conversion plotted against pressure at reaction conditions of 280° C., residence time of 0.5 hour, and C₃/CPD/MNB ratios of 2/1/0 and 2/1/1.
Figure 3:
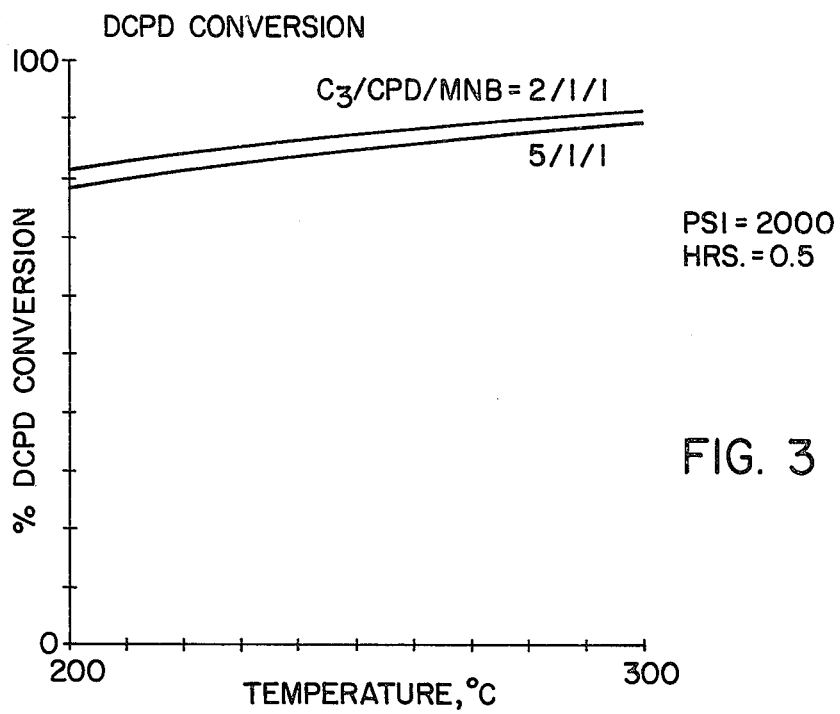
FIG. 3 is a plot of DCPD conversion against temperature at reaction conditions of 2000 psi, 0.5 hour residence time, and C₃/CPD/MNB ratios of 2/1/1 and 5/1/1.

It is evident from FIGS. 1 and 2 that DCPD conversion increased with residence time and pressure, and FIG. 3 confirms increased DCPD conversion at higher temperatures. FIG. 3 shows that DCPD conversion also increased with decreasing C$_3$/CPD/MNB ratios. For FIGS. 1 and 2, the temperature was 280° C., and the C$_3$/CPD/MNB mole ratios are 2/1/0 and 2/1/1. Residence time was kept constant at 0.5 hour for FIGS. 2, 3 and 4 whereas pressure for FIGS. 1, 3 and 4 was 2000 psi.

Figure 4:
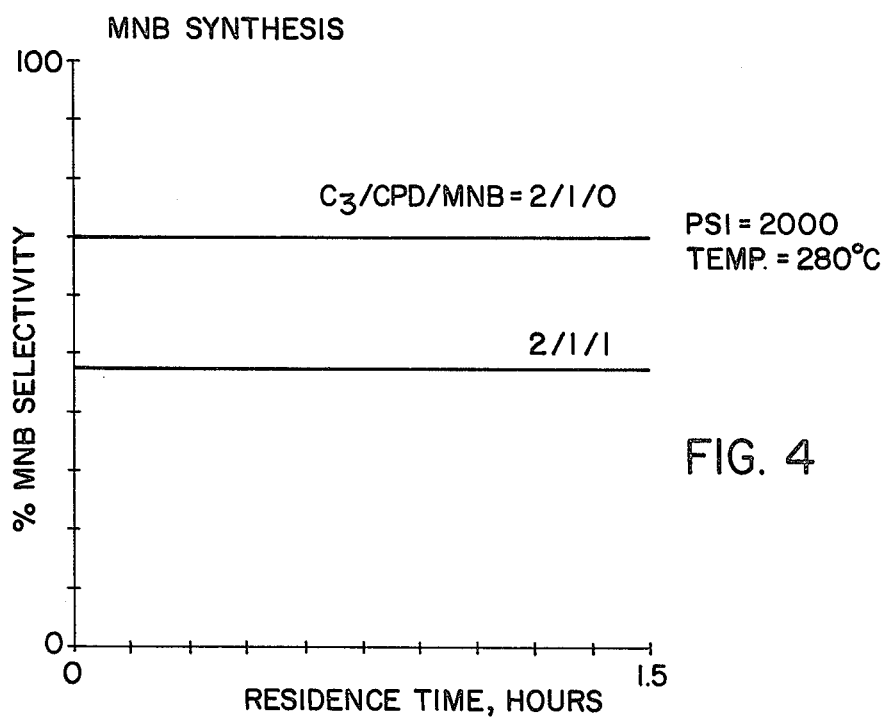
FIG. 4 is a plot of methylnorbornene (MNB) selectivity versus residence time in the reactor at reaction conditions of 280° C., 2000 psi and C₃/CPD/MNB ratios of 2/1/0 and 2/1/1.
Figure 5:
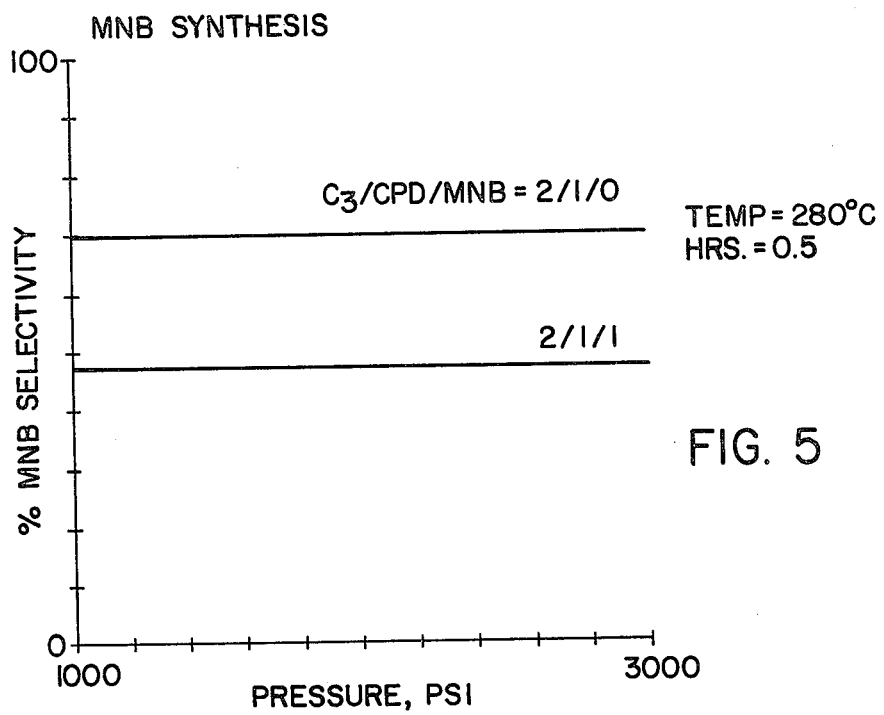
FIG. 5 is a plot of MNB selectivity versus pressure at reaction conditions of 280° C., 0.5 hour residence time and C₃/CPD/MNB ratios of 2/1/0 and 2/1/1.
Figure 6:
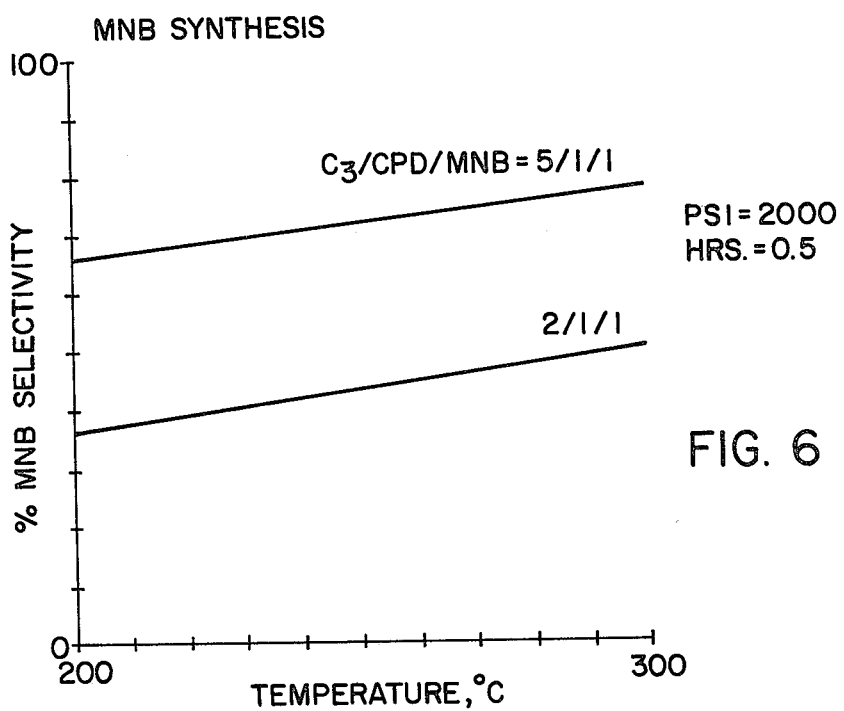
FIG. 6 is a plot of MNB selectivity versus temperature at reaction conditions of 2000 psi, 0.5 hour residence time and C₃/CPD/MNB ratios of 2/1/1 and 5/1/1.

As is evident from FIGS. 4 and 5, varying the residence time or the pressure did not affect MNB selectivity, however, MNB selectivity increased with increasing temperature and increasing C$_3$/CPD/MNB ratios, see FIG. 6. MNB selectivity was generally lower in the presence of precharged MNB due to MTD formation.

Figure 7:
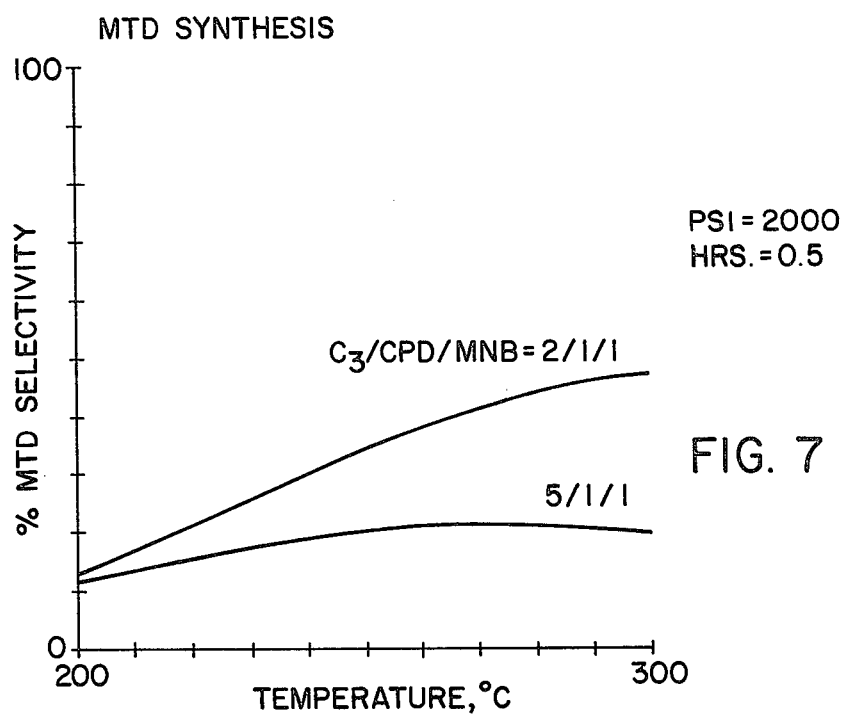
FIG. 7 is a plot of methyltetracyclododecene (MTD) selectivity versus temperature at reaction conditions of 2000 psi, 0.5 hour residence time and C₃/CPD/MNB ratios of 2/1/1 and 5/1/1.

FIG. 7 shows that MTD selectivity increased with temperature and decreasing C$_3$/CPD/MNB ratios. In presence of MNB and at low propylene levels, 50% to 80% of MTD was formed. When MTD selectivity rose, the MNB selectivity dropped. Low propylene concentration and high DCPD and MNB levels favored MTD formation.

Figure 8:
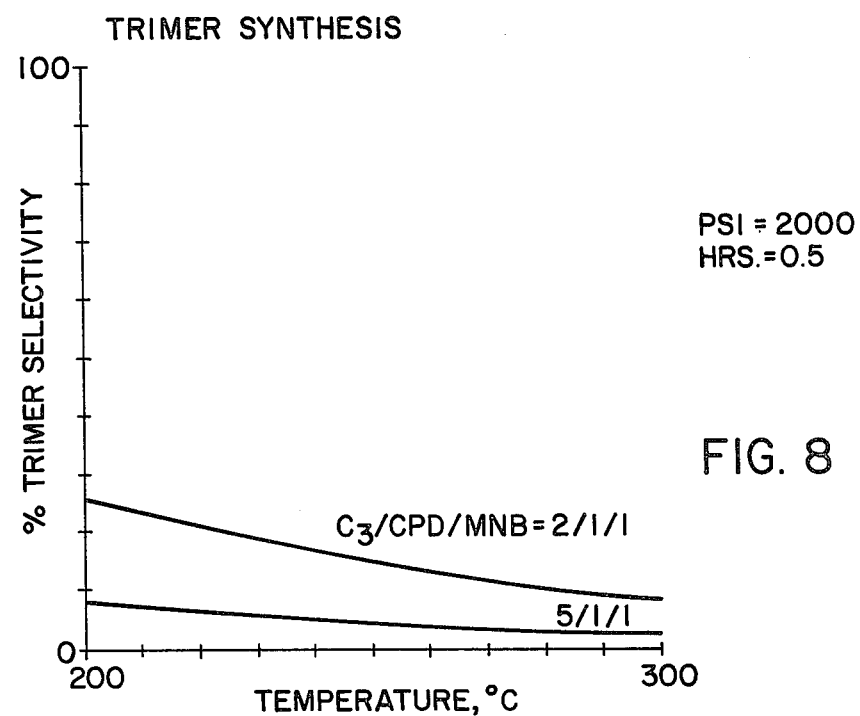
FIG. 8 is a plot of trimer selectivity versus temperature at reaction conditions of 2000 psi, 0.5 hour residence time and C₃/CPD/MNB ratios of 2/1/1 and 5/1/1.

FIG. 8 shows variation of trimer selectivity. With increasing temperature and increasing C3/CPD/MNB ratios, the trimer selectivity decreased. Trimer is an undesirable by-product which can be recycled, along with the other high boilers.

I claim:

1. A process for preparing a product mixture containing a norbornene and a tetracyclododecene in a desired molar ratio which is in the range of about 95/5 to 5/95 comprising heating in a reactor an olefin of 2 to 22 carbon atoms, a cyclopentadiene or a dicyclopentadiene, and a norbornene; maintaining ratio of reactants, temperature, pressure, and residence time in the reactor such that formation of the norbornene and the tetracyclododecene is favored; and recovering the norbornene and the tetracyclododecene from the product mixture.

2. Process of claim 1 wherein the olefin is selected from monoolefins and diolefins of 2 to 12 carbon atoms, and the norbornene and the tetracyclododecene are defined respectively as follows:

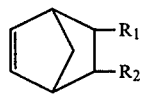 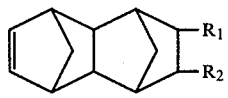

where $R_1$ and $R_2$ are independently selected from hydrogen, alkyl and alkylene groups of 1 to 20 carbon atoms, provided that total number of carbon atoms for $R_1$ and $R_2$ does not exceed 20; and where $R_1$ and $R_2$, together with the ring carbons to which they are bonded, form one or two saturated or unsaturated rings of 6 to 16 carbon atoms.

3. Process of claim 3 wherein $R_1$ and $R_2$ are independently selected from hydrogen, alkyl and alkylene groups of 1 to 10 carbon atoms.

4. Process of claim 3 wherein the olefin contains 2 to 4 carbon atoms; and $R_1$ and $R_2$ are individually selected from hydrogen and alkyl groups of 1 to 2 carbon atoms, provided that one of $R_1$ and $R_2$ is hydrogen.

5. Process of claim 3 wherein temperature of the reaction is in the range of 100° to 400° C., pressure is 100 to 5000 psi, and residence time of 0.1 to 5 hours.

6. Process of claim 4 wherein the reaction is carried out at a temperature of 200° to 300° C., pressure of 500 to 4000 psi, and residence time of 0.5 to 2 hours.

7. Process of claim 3 wherein the relative ratio of the reactants is as follows: 1 to 20 moles of the olefin, 1 to 5 moles of cyclopentadiene or one-half of this amount of dicyclopentadiene, and 1 to 5 moles of the norbornene.

8. Process of claim 4 wherein the relative ratio of the reactants is as follows: 2 to 10 moles of the olefin, 1 to 5 moles of cyclopentadiene or one-half of this amount of dicyclopentadiene, and 1 to 5 moles of the norbornene.

9. Process of claim 8 wherein the reaction is conducted at a relatively high temperature of the range of 100° to 400° C., relatively low olefin level, relatively high cyclopentadiene or dicyclopentadiene level, and relatively high norbornene level to produce mostly the tetracyclododecene.

10. Process of claim 9 which includes the step of recycling a portion of the norbornene to the reactor.

11. Process of claim 6 which includes step of recycling a portion of the norbornene to the reactor, the quantity of recycled norbornene being sufficient to maintain the process on a continuous basis.

12. Process of claim 11 wherein the reaction is carried out at 240° to 280° C. and about 2000 psi.

* * * * *